United States Patent [19]

Gump

[11] Patent Number: 4,656,008
[45] Date of Patent: Apr. 7, 1987

[54] ALCOHOL BREATH TESTING DEVICE

[75] Inventor: Jesse F. Gump, Maineville, Ohio

[73] Assignee: Alcolert Inc., Ohio

[21] Appl. No.: 658,118

[22] Filed: Oct. 5, 1984

Related U.S. Application Data

[63] Continuation-in-part of Ser. No. 505,772, Jun. 20, 1983, abandoned.

[51] Int. Cl.$^4$ .................................................. G01N 21/78
[52] U.S. Cl. ........................................ 422/86; 128/719; 436/132; 436/900
[58] Field of Search ............... 116/202, 286, 310, 334, 116/335; 128/716, 719, 720, 725–730; 422/55, 56, 58, 59, 84–88; 436/132, 167–169, 900, 902; 272/99; 356/421–423, 70; 362/23, 208, 253

[56] References Cited

U.S. PATENT DOCUMENTS

| | | | |
|---|---|---|---|
| 1,924,024 | 8/1933 | Carlson | 362/253 X |
| 2,291,562 | 7/1942 | Reysa et al. | 356/70 |
| 3,009,786 | 11/1961 | Luckey | 422/85 |
| 3,196,689 | 7/1965 | Forrester et al. | 422/85 X |
| 3,223,488 | 12/1965 | Luckey | 436/132 X |
| 3,635,214 | 1/1972 | Rand et al. | 128/727 |
| 4,063,821 | 12/1977 | King et al. | 356/167 |
| 4,298,010 | 11/1981 | Eckstein et al. | 128/719 |
| 4,444,202 | 4/1984 | Rubin et al. | 128/725 |
| 4,459,266 | 7/1984 | Lamoreaux | 128/719 X |

FOREIGN PATENT DOCUMENTS 379304  8/1932  Sweden .................... 422/86

Primary Examiner—Barry S. Richman
Assistant Examiner—Gzybowski, Michael S.
Attorney, Agent, or Firm—Wood, Herron & Evans

[57] ABSTRACT

An alcohol breath testing device comprising a conduit through which human breath air is passed. The conduit contains a chemical material which changes appearance upon being contacted by alcohol vapor. An air float chamber is operably connected to said conduit and has an air valve. The air chamber, air valve, and conduit are designed so that in a predetermined period of time a predetermined amount of breath air is permitted to pass through said device. The linear extent of color change in the chemical material in said predetermined period of time correlates to the concentration of alcohol in said breath air.

3 Claims, 9 Drawing Figures

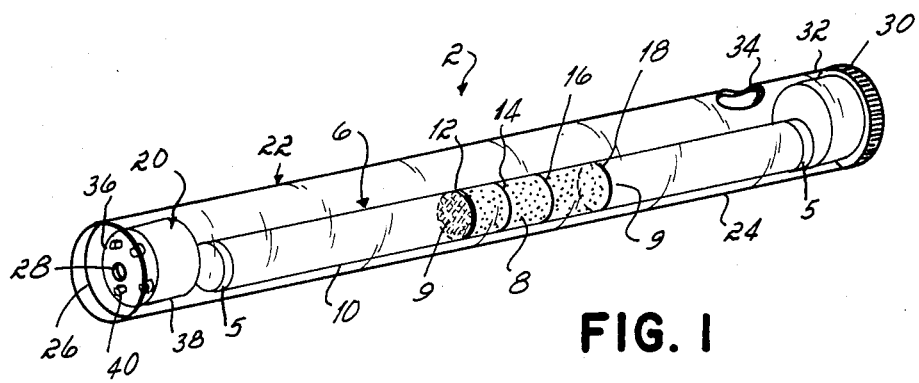
FIG. 1
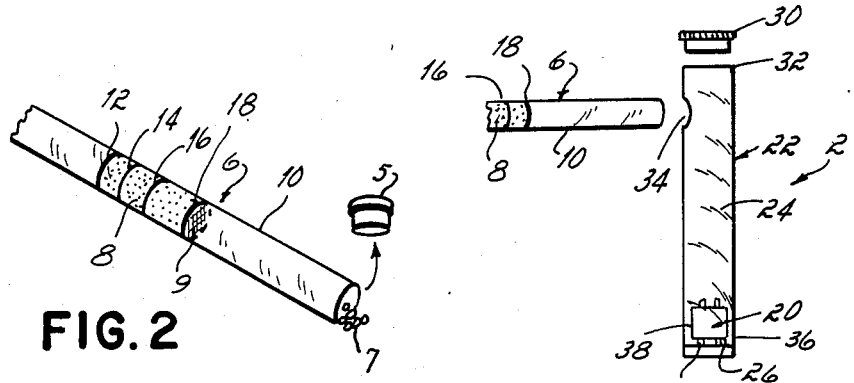
FIG. 2
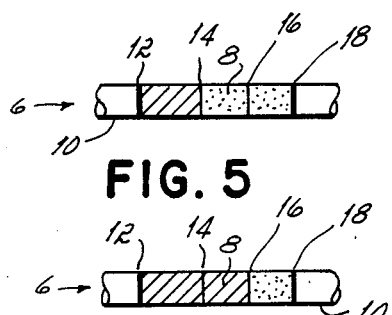
FIG. 3
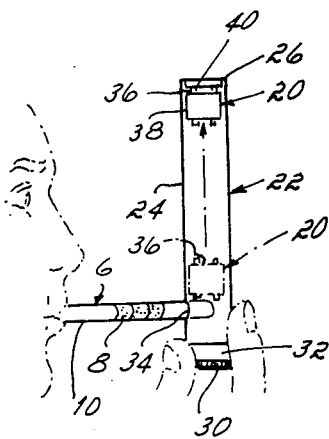
FIG. 4
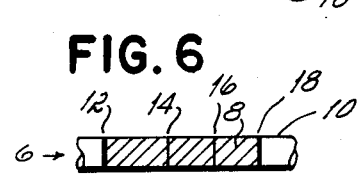
FIG. 5
FIG. 6
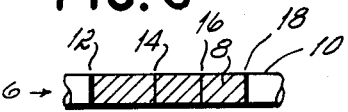
FIG. 7

ALCOHOL BREATH TESTING DEVICE

CROSS REFERENCE TO RELATED APPLICATIONS

This application is a continuation-in-part of my U.S. patent application Ser. No. 505,772 filed June 20, 1983, now abandoned.

BACKGROUND OF THE INVENTION

The present invention relates to an alcohol breath testing device intended for determining the alcohol concentration in air exhaled from human lungs.

The catastrophic consequences of driving vehicles while under the influence of alcohol are well known. In recent years concerted efforts have been made by various organizations, law enforcement agencies, and federal and state legislation, to reduce the number of people driving while under the influence. As a consequence, many states have now adopted laws which define alcohol intoxication in terms of the concentration of alcohol in one's breath. As a result of this increased effort to reduce alcohol related accidents through the stringent enforcement of laws prohibiting driving while under the influence of alcohol, a need has arisen for an accurate, inexpensive breath alcohol detection device that may be utilized by a motorist to determine whether or not the concentration of alcohol in his body exceeds a legal maximum concentration.

Devices attempting to satisfy the foregoing need are known, for example, such devices which attempt to measure alcohol concentration in one's breath are disclosed in U.S. Pat. Nos. 3,223,488, 3,917,456, and 4,329,318. While these devices are useful for the intended purpose, there still exists a need for such a device which is inexpensive, easily used, and which is accurate. There also exists a need to improve upon alcohol detection devices which do not include any means for accurately determining and/or controlling the amount of expelled breath air that must be passed through the device in order to accurately determine alcohol concentrations. A need also exists to eliminate in some devices the air balloon that is used to provide a way of providing a measured amount of breath air for alcohol concentration measurement. This need arises due to the inaccuracies inherent in such use, the cumbersome nature of such devices, and through the need to provide a simpler device.

There has also been a need to provide such a device which includes an integral illumination means to enable the user to read the alcohol concentration that is displayed.

It has been therefore one objective of my invention to provide an alcohol breath detection device which is inexpensive, simple to use, and accurate.

It has been another objective of this invention to provide such a device which includes means which will simply and accurately permit a predetermined amount of air expelled from the lungs to be introduced into said device and passed through the chemical composition in a predetermined period of time.

It has also been the objective of one embodiment of this invention to provide a device which can be illuminated for nighttime use and which may be reused by inserting a new chemical containing capsule or conduit.

SUMMARY OF THE INVENTION

The foregoing objectives and needs have been satisfied by the present invention which includes, in combination, a breath air conduit which includes a chemical material that changes appearance upon exposure to alcohol in breath air, an air float chamber operably attached to the air conduit which chamber includes an air valve. As used herein breath air refers to the air expelled from one's lungs. The chemical composition disclosed changes colors in a linearly progressive manner. Indicia on the conduit walls display the alcohol concentration. The air chamber and air float enable the user to introduce into the device a predetermined amount of air over a predetermined period of time. The air float is propelled or moved from an at rest position of non-use to a second, in use position through the input of breath air into the conduit. A predetermined velocity of air is required to maintain the air float in the second, use position. When this velocity is not maintained the air valve does not stay in the desired second position. Through the air chamber-air float mechanism a known amount of breath air may be introduced in a given period of time thus providing a sample whose concentration of alcohol may be accurately determined.

These and other objectives will become apparent from the accompanying description and drawings wherein:

FIG. 1 is a schematic perspective view of a disposable alcohol breath testing device;

FIGS. 2, 3 and 4 are sequential steps utilized in preparing the device of FIG. 1 for use;

FIG. 5 is a readout obtained by use of the invention illustrating that the user's motor reflexes are impaired;

FIG. 6 is a view similar to FIG. 5 but indicating that the user is legally intoxicated;

FIG. 7 is a view similar to FIGS. 5 and 6 except the readout illustrates the user is totally impaired;

DESCRIPTION OF THE PREFERRED EMBODIMENTS

Figure 8:
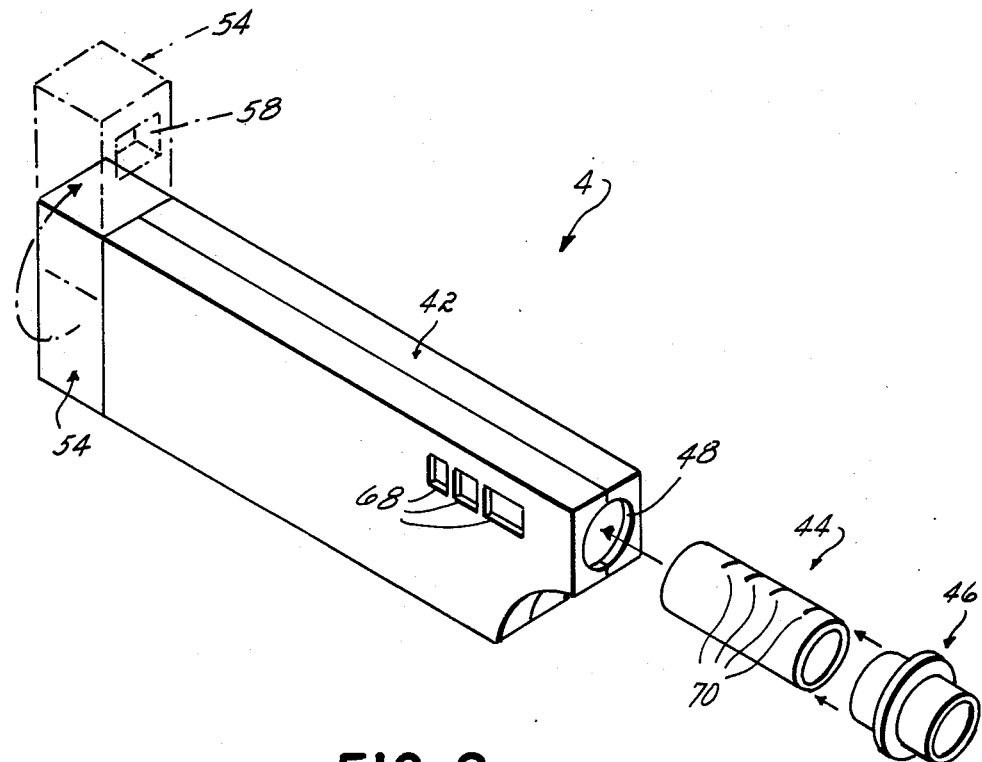
FIG. 8 is an exploded perspective view illustrating a reusable alcohol breath testing device.

Described hereinafter are two different embodiments of my invention, one, a disposable unit generally referred to by the number 2, and a reuseable unit 4. While they differ substantially in certain respects, their principals of operation and their principal mechanical elements insofar as alcohol concentration measurement is concerned are substantially the same.

Referring to FIGS. 1-7 the nonreusable unit 2 will first be described. This unit includes a cylindrical shaped breath air conduit 6 which is approximately 4 inches long and approximately ⅜ inches in diameter. Preferably the conduit 6 is made from transparent plastic. If desired it could have a different cross-sectional shape. Packed into the conduit 6 is a chemical material 8 which changes appearance, i.e. color, upon exposure to alcohol in breath air. Various chemical materials suitable for use are known, as for example those discussed in U.S. Pat. No. 3,223,488. One that has been found to be suitable is one made from:

2 ML $H_2O$
8 ML $H_2SO_4$ (95% concentration reagent grade)
0.085 grams sodium dichromate When exposed to alcohol vapors this material changes from its normal yellow color to green. When packed into the conduit 6 the amount of chemical material just described will fill about 1" of the conduit 6. This amount preferably is inserted into the middle of the conduit 6 and is contained by small plastic screens 9 which are pressure fit into the conduit and by conduit walls 10. The opposed ends of the conduit 6 are filled with a silica gel desicant material 7 to preserve the life of the chemical, the material 7 being retained by end plugs 5. Indicia, as for example printed lines 12, 14, 16, 18 are included on the walls 10 with the first line 12 at one end of the chemical material 8 and the last line, i.e. 18, at the opposite end of the chemical material 8. Intermediate lines 14 and 16 are provided to indicate different alcohol concentrations in a manner to be more fully described. The amount and length of the chemical material 8 was selected so that the concentration of alcohol in a known volume of breath air, i.e. about 800 cc, can be ascertained. For example, a change of the chemical material from yellow to green between lines 12-14 (FIG. 5) signals a 0.05 alcohol concentration. If the yellow changes to green between lines 12 to line 16 a 0.10 level is indicated (FIG. 6). FIG. 7 illustrates a concentration of 0.15. These levels were selected because in many states a 0.10 level indicates that the user is legally intoxicated. A level of 0.15 normally indicates total impairment. Obviously other levels could also be shown.

To calibrate the device and insure accuracy empirical measurements were made as follows. A male weighing approximately 160 pounds consumed three regular, 12 ounce bottles of beer within half an hour (½ hour), a blood sample was taken, and the concentration of alcohol determined by a known, accepted list procedure. A measured quantity of air of about 800 cc was obtained which when passed through the conduit 6 and chemical material 8 produced a linear color change of the chemical material 8. This linear change was considered to indicate a concentration equal to the concentration determined from the blood test and the walls 10 of conduit 6 were marked accordingly.

An air valve 20 housed in an air valve chamber 22 is used to insure that the predetermined amount of breath air (approximately 800 cc) is passed through the device in a predetermined amount of time, i.e., about 15 seconds. Without such means the quantity of air would vary depending on the pressure one exerts in exhaling one's breath air which controls the velocity of the air. This is undesirable since the linear extent of color change varies with total alcohol vapors passing through the device. Therefore, to get an accurate analyses, a precise amount must be introduced. Air balloons attempted to accomplish this objective in some prior art devices but have not been entirely successful.

The air valve chamber 22 illustrated in FIGS. 1-4 is tubular shaped, about 5 inches long with an inside diameter of 0.604 and an outside diameter of 0.632. It is made from transparent plastic and has side walls 24 and an end wall 26 which has an aperture 28 of about ⅛ inch therethrough. A plastic stopper 30 is used to provide a removable sealing mechanism at the end 32 opposite the aperture 28. This end 32 contains a hole 34 having a diameter slightly larger than the outer diameter of the conduit 6 for purposes that are discussed below. The cross-sectional shape of the air valve chamber 22 can vary and need not be circular. If a non-circular shape is used the shape of hole 34 will have have a corresponding shape.

The air valve 20 is cylindrical and has a top wall 36 and side walls 38. The air valve 20 weighs about 0.7 grams. The air valve 20 includes four posts 40 on the top wall 36. These insure that when the air valve 20 is inserted in the air valve chamber 22 (See FIGS. 1 and 4) the top wall 36 does not obstruct the aperture 28. The outside diameter of the air valve 20 is 0.530, which is slightly less than that of the air chamber 22 so that air can pass between the chamber side walls 24 and the side walls 38 of the air valve 22.

The diameter of aperture 28, distance between the side walls 38 and side walls 24, the weight of the air valve 20, the diameter of the conduit 6, and the diameter of the air valve chamber 22, were selected so that when properly used there would be introduced the predetermined quantity of breath air would pass through the unit. More particularly, when used, the stopper 30 and conduit 6 are removed from the air valve chamber 22, the conduit 6 is emptied of desicant 7 (FIG. 2) and then inserted into the hole 34, and the stopper 30 replaced. The insertion of conduit 6 is done with the chamber 22 inverted so that valve 20 will reside above the conduit 6 when the chamber is turned upright. This procedure is most easily accomplished in the manner illustrated in FIG. 3. Next the stopper 30 is installed and the unit is placed in the position of FIG. 4 and the user blows into the conduit 6. A proper and predetermined velocity of breath air causes the air valve 20 to move from its position above conduit 6 adjacent the bottom of the air chamber 22 (FIG. 4) to the end wall 26 adjacent to the aperture 28. Breath air passes out through aperture 28. The air valve 20 is held against end wall 26 for 15 seconds by blowing. The change in color of the chemical material 8 is noted as is the linear extent of the changes. In order to obtain an accurate reading the air valve 22 must be forced and held against the end wall 26 for the predetermined time. The use of the transparent plastic enables the user to see that the air valve 20 is positioned properly.

Figure 9:
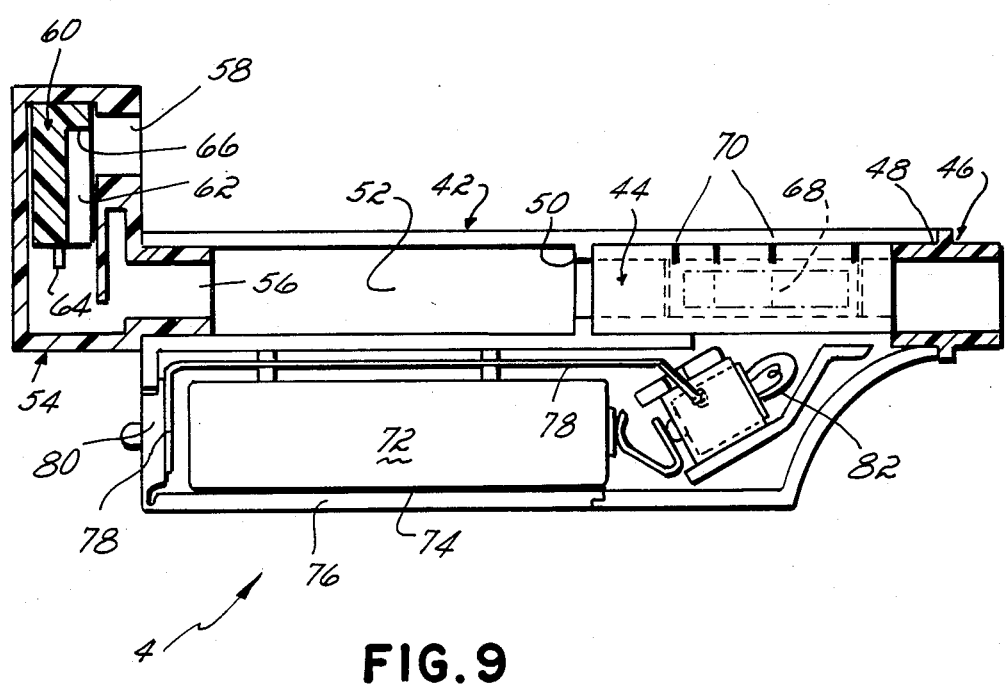
FIG. 9 is an assembled longitudinal cross-sectional view through the device of FIG. 8 illustrating the position of the components during the use of the invention.

The reuseable unit 4 is best understood by reference to FIGS. 8 and 9. It, too, uses a breath air conduit, chemical material, air valve and air valve chamber, but in this embodiment they are structurally different. These differences and other features unique to this unit will now be discussed.

A molded plastic, two piece, case 42 provides an enclosure for a small replaceable breath air conduit 44 which contains the same type of chemical material heretofore described. The conduit contains indicia for reading alcohol content. A removable mouthpiece 46 fits into a hole 48 the end of the case after the conduit 44 is inserted. Referring to FIG. 9 where one piece of the case 42 is shown with the other half removed, the mouthpiece 46 is shown inserted and the conduit 44 is shown in phantom place. A retaining ring 50, molded into the case, and the mouthpiece 46 insure that the conduit is secured against movement after their insertion. Breath air passageway 52 permits air leaving conduit 44 to be directed toward a rectangular shaped, rotatable, air valve chamber 54. Air enters the chamber 54 through a circular throat 56 and out exit passageway 58. The throat 56, slightly smaller than the diameter of the passageway 52, is sized to provide a snug fit so that the chamber 54 is not too easily removed from the case 42. The fit does permit the chamber 54 to swivel from a raised position for usage to a lowered position for storage, as shown in FIG. 8. An air valve 60, shown in cross section in FIG. 9, is generally rectangular and contains an air slot 62 which permits air to pass through it and out air passageway 58 when the air valve 60 is raised by the breath air passing through the conduit 44, passageway 52 and throat 56. Two feet 64, one at each side of the air valve 60, hold the air valve 60 slightly above the bottom of the air valve chamber 54 so that breath air can force the valve 60 upwardly when it impacts on the valve 60 by striking the top wall 66 at the slot 62. Again, as before, this unit 4 is designed so that in a given period of time a predetermined amount of air may be blown through the unit when the air valve 60 is in the operating position shown in FIG. 9. Likewise, the device is calibrated in the manner previously described so as to be able to measure the concentration of alcohol in that predetermined amount of breath air.

Apertures 68 in the case 42 enable the reader to view the chemical material and indicia 70 on conduit 44 after usage. If desired, passageway 52 provides a storage chamber for additional conduits 44 by removal of the air valve chamber 54.

An important feature of this reusable unit 4 is the provision of a battery operated light so that the unit can be easily used at night. A battery 72 fits within battery chamber 74. Access is provided through a hinged door 76. Operably connected to the battery 72 through a conventional spring 78 and push contact switch 80 is a light 82. Pushing on the contact switch 80 closes the circuit and causes the battery 72 to light the light 82 which illuminates the conduit 44.

Having thus described my invention, I claim:

1. A device for detecting the concentration of alcohol in a human breath sample, comprising:

an air chamber having a bottom, comprising a removable bottom member, and a top and at least one sidewall therebetween, said air chamber having a first aperture located in said at least one sidewall near said bottom and a second aperture located in said top whereby breath air may pass through the air chamber;

a conduit removably stored within said air chamber and removable through said air chamber bottom, said conduit having a first forward end and a second rearward end, said rearward end removably, operably connectable to said air chamber being receivable in said first aperture, said forward end receivable in a human's mouth to permit breath air to be coupled directly from the human through said conduit and into said air chamber when said conduit is operably connected to said air chamber;

a chemical material positioned within said conduit which, as breath air passes therethrough, changes color linearly from one end of the material spaced forwardly in the conduit towards an end of the material spaced rearwardly in the conduit as the concentration of alcohol passed therethrough increases;

indicia on said conduit which cooperate with said chemical material to indicate, after use, the concentration of alcohol in said breath air;

said air chamber including therein an air float movable, by breath air coupled into said air chamber, between a first position spaced near said bottom and a second, operative position whereat a portion of the air float contacts said top of said air chamber, said air float, said top of said air chamber, said second aperture and said at least one sidewall cooperating, when said air float is in said operative position, to define means for limiting velocity of said breath air to a predetermined velocity when the human blows breath air through said conduit with sufficient exertion to otherwise exceed said predetermined velocity.

2. The device of claim 1 wherein said at least one sidewall is cylindrical.

3. A device for detecting the concentration of alcohol in a human breath sample, comprising:

a housing having an inlet receivable in the human's mouth and an air chamber for receiving breath air therethrough;

said air chamber being rotatable between a closed position and an open position and having a bottom and a top, said air chamber being coupled to an air passageway within said housing between said inlet and said air chamber to couple breath air to said air chamber through an aperture near said bottom, said air chamber including means near said top to permit egress of breath air from said air chamber only in said open position;

a conduit having a first forward end and a second rearward end removably receivable within said housing, said rearward end operably connectable to said air passageway, said forward end couplable to said inlet to permit breath air to be coupled directly through said conduit and into said air chamber;

a chemical material positioned within said conduit which, as breath air passes therethrough, changes color linearly from one end of the material spaced forwardly in the conduit towards an end of the material spaced rearwardly in the conduit as the concentration of alcohol passed therethrough increases;

indicia on said conduit which cooperate with said chemical material to indicate, after use, the concentration of alcohol in said breath air, said housing including viewing ports to permit viewing of said chemical material and said indicia;

battery operated light means selectively operable for illuminating said indicia and chemical material to assist in viewing thereof;

said air chamber including therein an air float movable between a first position spaced near said bottom and a second position spaced near said top, said air float being in said first position in the absence of breath air passing through said air chamber and said air chamber being in said open position, said air float being in said second position when breath air passes through said air chamber at a predetermined velocity and said air chamber being in said open position, said air float further being in said second position when said air chamber is in said closed position, said air float, said top and said breath air egress means cooperating, when said air float is in said second position, to define means operable when said air chamber is in said open position for limiting velocity of said breath air to said predetermined velocity when the human blows breath air through said conduit with sufficient exertion to otherwise exceed said predetermined velocity.

* * * * *